(12) United States Patent
Shtyrlin et al.

(10) Patent No.: US 10,507,202 B2
(45) Date of Patent: Dec. 17, 2019

(54) NAPROXEN-BASED NON-STEROIDAL ANTI-INFLAMMATORY DRUG WITH LOW GASTRIC TOXICITY

(71) Applicants: AO "TATKHIMFARMPREPARATY", Kazan (RU); Kazan Federal University, Kazan (RU)

(72) Inventors: Yurij G. Shtyrlin, Kazan (RU); Roman S. Pavel'Ev, Kazan (RU); Al'fiya G. Iksanova, Kazan (RU); Nikita V. Shtyrlin, Kazan (RU); Mikhail V. Pugachev, Ul'yanovsk (RU); Konstantin V. Balakin, Moskovskaya Obl. (RU); Aleksandr M. Ajmaletdinov, Kazan (RU); Il'nur M. Ganiev, Tatarstan (RU); Al'bina G. Malan'Eva, Kazan (RU)

(73) Assignees: AO "Tatkhimfarmpreparaty", Kazan (RU); Kazan Federal University, Kazan (RU)

( * ) Notice: Subject to any disclaimer, the term of this patent is extended or adjusted under 35 U.S.C. 154(b) by 0 days.

(21) Appl. No.: 16/399,590

(22) Filed: Apr. 30, 2019

(65) Prior Publication Data

US 2019/0255030 A1 Aug. 22, 2019

Related U.S. Application Data

(63) Continuation of application No. PCT/RU2017/000808, filed on Oct. 31, 2017.

(30) Foreign Application Priority Data

Nov. 2, 2016 (RU) ................................ 2016143071

(51) Int. Cl.
*A61K 31/4412* (2006.01)
*A61P 29/00* (2006.01)

(52) U.S. Cl.
CPC .......... *A61K 31/4412* (2013.01); *A61P 29/00* (2018.01)

(58) Field of Classification Search
CPC .......................... A61K 31/4412; A61P 29/00
See application file for complete search history.

(56) References Cited

U.S. PATENT DOCUMENTS 4,260,613 A    4/1981  Reiner

FOREIGN PATENT DOCUMENTS

| EP | 2431361 A1 | 3/2012 |
| RU | 2513089 C1 | 4/2014 |
| WO | 2008101064 A1 | 8/2008 |

OTHER PUBLICATIONS

International Search Report from PCT/RU2017/000808, dated Oct. 31, 2017, dated Jan. 31, 2018.
Handa, et al., The impact of non-steroidal anti-inflammatory drugs on the small intestinal epithelium, J. Clin. Biochem. Nutr., Jan. 2014, pp. 2-6, v. 54, No. 1.
Singh, B.K. et al, Assessment of nonsteroidal anti-inflammatory drug-induced cardiotoxicity, Expert Opin. Drug Metab. Toxicol., 2014, pp. 143-156, v. 10, No. 2.
Liu, W. et al., Synthesis and biological evaluation of curcumin derivatives containing NASAIDs for their anti-inflammatory activity, Bioorg. Med. Chem. Lett., 2015, pp. 3044-3051, v. 25.
Schwarts, G.Y.et al, Guidelines to the Pre-Clinical Study of Nonsteroidal Anti-inflammatory Drugs, Guidelines for conducting preclinical studies of drugs, 2012, Part One, Chapter 48, pp. 746-749, Ed. A.N. Mironov.—M.: Grief and K.
Mashkovsky, M. D., Medicines, 2012, p. 178, 16th Ed., Revised, Moscow: New Wave.
GOST 12.1.007-76 Harmful substances. Classification and general safety requirement, p. 2.

*Primary Examiner* — Yong S. Chong
(74) *Attorney, Agent, or Firm* — Patentbar International, P.C.

(57) ABSTRACT

A new derivative of naproxen, 3-((S)-2-(6-methoxynaphth-2-yl) propanoyloxy)-4,5-bis (((S)-2-(6-methoxynaphth-2-yl) propanoyloxy)-methyl)-2-methylpyridinium (S)-2-(6-methoxynaphth-2-yl) propanoate has a high anti-inflammatory, analgesic and antipyretic activity, as well as low acute toxicity and gastrotoxicity, it can be used in the pharmaceutical industry, medicine and veterinary.

1 Claim, No Drawings

NAPROXEN-BASED NON-STEROIDAL ANTI-INFLAMMATORY DRUG WITH LOW GASTRIC TOXICITY

RELATED APPLICATIONS

This application is a Continuation application of International Application PCT/RU2017/000808, filed on Oct. 31, 2017, which in turn claims priority to Russian Patent Application RU2016143071, filed Nov. 2, 2016, both of which are incorporated herein by reference in their entirety.

FIELD OF THE INVENTION

The invention relates to a new formula I naproxen derivative which has a high anti-inflammatory, analgesic and antipyretic activity, as well as low acute toxicity and gastrotoxicity and which can be used in the pharmaceutical industry, medicine and veterinary medicine.

The main element of the mechanism of action of NSAIDs is the suppression of the synthesis of inflammatory mediators—prostaglandins. During the process of alteration (the first stage of inflammation) the cell membrane releases phospholipids which under the action of the enzyme of phospholipase A2 are metabolized to arachidonic acid. Arachidonic acid, in turn, is metabolized in two ways: cyclooxygenase (COX) and lipoxygenase (LOX). NSAIDs inhibit only COX, so they block the development of only the second stage of inflammation [Guidelines for Pre-clinical Drug Research. Part one/edited by A. N. Mironov. —M.: Grif and K Publ., 2012. p. 944].

There are 2 COX isoenzymes: COX-1 (constitutional, normally existing) controls the production of prostanoids that regulate physiological functions of the stomach, vessels and kidneys; COX-2 (induced) is involved in the synthesis of prostaglandins in inflammation. COX-2 is normally absent and is formed under the influence of tissue factors that induce an inflammatory response (cytokines, etc.). It is

I

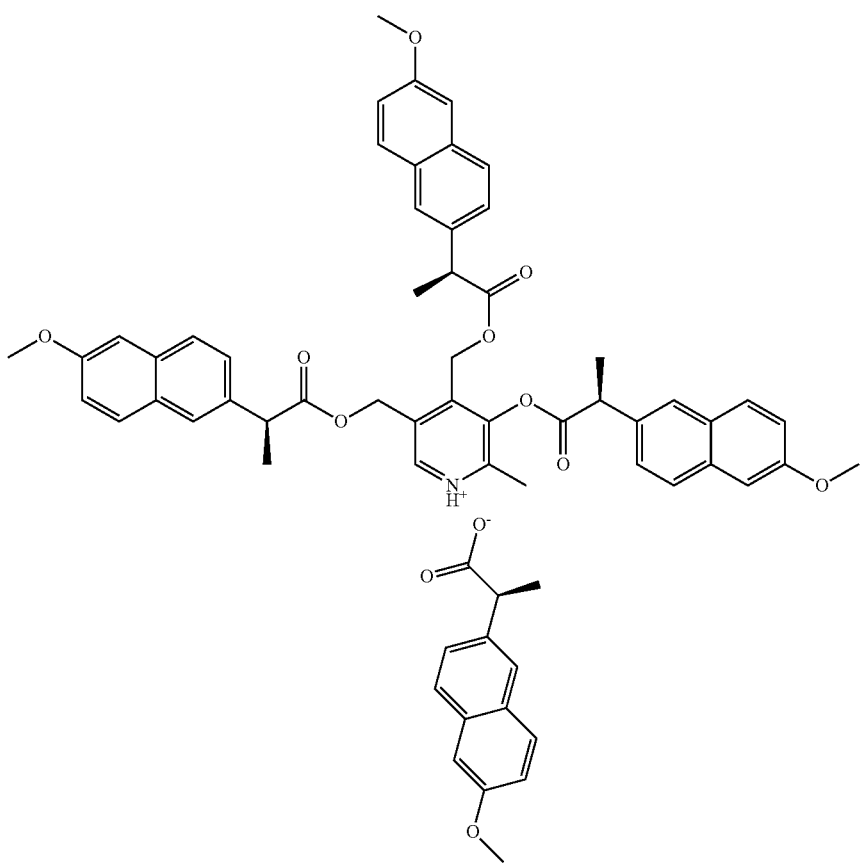

BACKGROUND OF THE INVENTION

The main indications for the prescription of non-steroidal anti-inflammatory drugs (hereinafter NSAIDs) are inflammatory processes of different nature and localization, pain and fever. NSAIDs are one of the most widely used groups of drugs. For example, NSAIDs are prescribed to about 20% of inpatients with various diseases of internal organs [Guidelines for Pre-clinical Drug Research. Part one/edited by A. N. Mironov.—M.: Grif and K Publ., 2012. p. 944].

believed that the anti-inflammatory effect of NSAIDs is due to the inhibition of COX-2, and the side effects are due to the inhibition of COX-1 [Guidelines for Pre-clinical Drug Research. Part one/edited by A. N. Mironov. —M.: Grif and K Publ., 2012. p. 944].

The most known NSAIDs are ketoprofen (3-benzoyl-alpha-methylbenzene acetic acid), ibuprofen ((RS)-2-(4-isobutylphenyl) propionic acid), diclofenac (2-[(2,6-dichlorophenyl) amino] benzene acetic acid), indomethacin (1-(4-chlorobenzoyl)-5-methoxy-2-methyl-1H-indol-3-acetic acid) and naproxen ((S)-6-methoxy-α-methyl-2-naphthalenacetic acid). Currently naproxen occupies one of the leading positions in the group of NSAIDs, because it has a longer effect than other NSAIDs and is well tolerated [Mashkovsky M. D. Lekarstvennye sredstva. [Medicinal Drugs.] 16th ed., revised and modified—M.: Novaya Volna [New Wave] Publ., 2012. p. 1216].

The disadvantage of known to date NSAIDs, namely non-selective cyclooxygenase inhibitors, is their pronounced gastric toxicity [Handa, O. The impact of non-steroidal anti-inflammatory drugs on the small intestinal epithelium/O. Handa, Y. Naito, A. Fukui, T. Omatsu, T. Yoshikawa//J. Clin. Biochem. Nutr.—2014.—V. 54, N. 1.—P. 2-6.]. Selective inhibitors of COX-2 are less gastrotoxic, but their negative effects on the cardiovascular system are known [Singh, B. K. Assessment of nonsteroidal anti-inflammatory drug-induced cardiotoxicity/B. K. Singh, S. E. Hague, K. K. Pillai//Expert. Opin. Drug Metab. Toxicol.—2014.—V. 10, N. 2.—P. 143-156.]. Thus, on the date of submission of the application materials, the problem of reducing the side effects of both types of NSAIDs—selective and non-selective cyclooxygenase inhibitors—remains unresolved.

Thus, the development of safe and effective NSAIDs is one of the most important tasks of pharmacotherapy and health care in general.

In the applicant view, based on the analysis of the level of technology, the most promising direction of development of anti-inflammatory drugs is search for non-selective NSAIDs. At the same time, as noted above, developers face the task of reducing side effects, the main of which is gastric toxicity.

Protection of carboxyl group of non-selective COX inhibitors is one of the main ways to reduce toxicity of this group of NSAIDs. Ester protection is the most frequently used for this purpose [Liu, W. Synthesis and biological evaluation of curcumin derivatives containing NSAIDs for their anti-inflammatory activity [Text]/W. Liu, Y. Li, Y. Yue, et al.//Bioorg. Med. Chem. Lett.—2015.—V. 25, N. 15.—P. 3044-3051.]. NSAIDs esters are typical promedications, which in the gastrointestinal tract (hereinafter referred to as the GIT) undergo enzymatic hydrolysis with gradual release of NSAIDs, providing a prolonged effect of the drug. In addition, promedications based on esters better penetrate cytoplasmic membranes of cells, thus having less irritating effect on the mucous membrane of the GIT. Ascorbic acid esters with NSAIDs are known to be derivatives of arilacetic or arylpropionic acids, such as ibuprofen, ketoprofen, naproxen and their salts [EP 2431361, published on 21 Mar. 2012]. For the treatment of arthritis, pain and inflammatory processes was proposed 2-methansulfonatethyl ester of naproxen together with H2 receptors antagonist [WO 200810106441, published 21 Aug. 2008]. This modification of NSAIDs leads to a decrease in gastric toxicity, but at the same time significantly reduces the therapeutic effect. For this reason, these compounds have not been included in clinical practice.

The closest combination of coinciding features and achieved technical result to the claimed invention is the technical solution described in the invention in the patent RU 2513089 "Non-steroidal anti-inflammatory drugs based on pyridoxine derivatives", the essence of which are pyridoxine derivatives of the general formula (I)

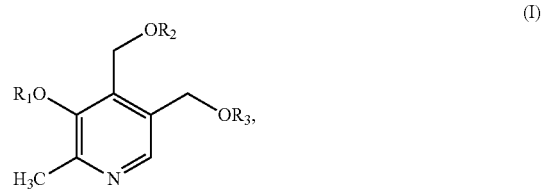

where:
when $R_2+R_3$=—C(CH$_3$)$_2$— or —CH (CH$_3$)—;

$R_1$ = 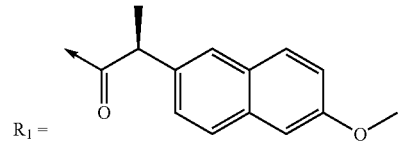

when $R_1$=H; $R_3$=H;

$R_2$ =

$R_1 = R_2 = R_3 = $ 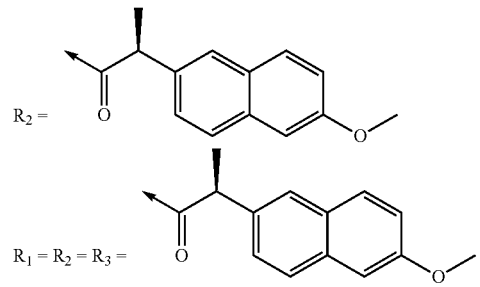

having anti-inflammatory activity.

The prototype version containing three fragments of naproxen is an effective anti-inflammatory compound. In particular, it has a pronounced anti-inflammatory effect on the model of subacute (formalin) edema in vivo.

However, on the model of acute (carrageenin) edema in vivo this prototype was not effective enough. It is important to note that the prototype does not have at the same time a set of properties of the claimed invention, namely high anti-inflammatory (on the model of acute (carrageenin) edema in vivo), analgesic and antipyretic activity combined with low toxicity, including gastric toxicity. For this reason, the applicant does not consider this prototype as a comparison drug, instead of it a modern non-steroidal anti-inflammatory drug naproxen and its analogues are used for this purpose (table 3).

The claimed composition of the claimed invention differs from that described in the prototype by the presence of an additional fragment of naproxen, which, in the applicant's experimentally grounded view, causes the appearance of pharmacologically significant positive effects. Thus, the combination in the claimed molecule of covalent ester bonds split under physiological conditions and non-covalent ionic bond linking fragments of naproxen and pyridoxine, leads to the emergence of synergistic effects that are not obvious to a specialist. These effects are expressed in increased anti-inflammatory, analgesic and antipyretic activity, as well as in significantly reduced gastric toxicity and acute toxicity. In particular, the claimed compound of formula I against the background of reduced gastric toxicity and acute toxicity ensures a rapid onset of a pronounced anti-inflammatory effect on the model of both acute and subacute edema in vivo, whereby the applicant can resolve the seemingly insurmountable problem typical of both the prototype and many other NSAIDs including naproxen (the latter is also the prototype of the claimed invention).

SUMMARY OF THE INVENTION

The objective of the claimed invention is to create a pharmaceutical drug based on naproxen, which has a high anti-inflammatory, analgesic and antipyretic activity in combination with low toxicity, including gastric toxicity, significantly expanding the arsenal of known means of the specified destination.

The technical result of the invention is a new non-steroidal anti-inflammatory drug based on pyridoxine and naproxen, exhibiting high anti-inflammatory, analgesic and antipyretic activity on the background of significantly lower toxicity, including gastric toxicity, compared with the known NSAIDs, including the prototype.

The problem is solved, and the claimed technical result is achieved by synthesizing a compound of formula I and using it as an anti-inflammatory, analgesic and antipyretic agent with reduced gastric toxicity:

Table 2—Acute toxicity of formula I compound in intragastric administration;

Table 3—Comparative characteristics of formula I compound and some known NSAIDs;

Table 4—Gastric toxicity of formula I compound with single administration at a dose of 2000 mg/kg;

Table 5—Effect of formula I compound on acute exudative inflammation in intragastric administration;

Table 6—Analgesic effect of formula I compound on rats;

Table 7—Antipyretic effect of formula I compound on rats.

Information confirming the composition and structure of the claimed compound is shown in the examples of specific performance. The structure of the obtained compound was confirmed by $^1$H and $^{13}$C NMR spectroscopy, UV spectroscopy, chromatography-mass spectrometry.

NMR spectra were recorded on the Bruker AVANCE-400 device. The chemical shift was determined with respect to the signals of residual protons of deuterated solvents ($^1$H and $^{13}$C). Melt temperatures of products were determined using Stanford Research Systems MPA-100 OptiMelt at a heating rate of 1° C./min. The UV spectrophotometer Evolution 300

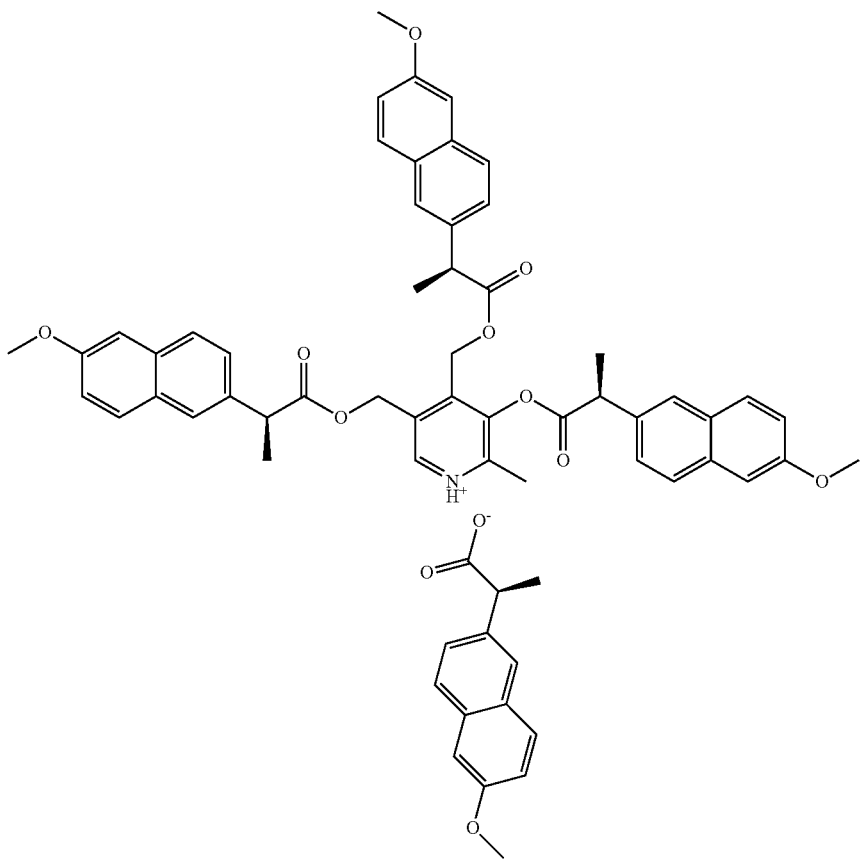

I

The claimed invention is illustrated by the following materials:

Reaction sequence—chemical reaction sequence of synthesis of formula I compound;

Table 1—Parameters of gradient elution mode at analytical HPLC;

(Thermo scientific) was used to study the spectral characteristics of the solutions of the formula I compound. Specific rotation was determined on the automatic polarimeter ADP440+(B&S) (England) using quartz matrix tube 100° Z. High-resolution mass spectra (HRMS) were recorded using TripleTOF 5600, AB Sciex (Germany) mass spectrometer from methanol solution by ionization—turboion spray (TIS)—at energy of impacts with nitrogen molecules equal to 10 eV.

Determination of purity of compound of formula I was performed by reverse phase HPLC using the values of the gradient elution mode of Table 1, using a high performance liquid chromatograph LCMS-2010EV, Shimadzu (Japan) equipped with a XBridge C18 diode array detector (size 4.6×50 mm, 3.5 μm). The temperature of the column thermostat is +40° C., the flow rate is 1 ml/min, the volume of the introduced sample is 1 mg/ml. UV detection was performed at an analytical wave length of 220 nm, as well as 254 and 330 nm to determine impurities. As a moving phase was used: channel A—0.1% by volume of formic acid in water, channel B—acetonitrile. The mode of operation of the pump is gradient elution, analysis time is 22 minutes.

TABLE 1

| Gradient elution mode parameters for analytical HPLC | |
|---|---|
| Time, min | Volume fraction of channel B component, % |
| 0.01 | 5 |
| 10.00 | 70 |
| 25.00 | 0 |

EXAMPLES OF SPECIFIC IMPLEMENTATION OF THE CLAIMED TECHNICAL SOLUTION

Obtaining the claimed compound of formula I containing fragments of pyridoxine (vitamin $B_6$) and naproxen is carried out in two stages using commercially available substrates, reagents and solvents according to the reaction sequence below.

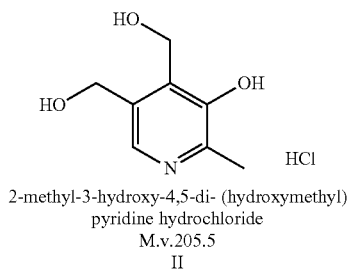

2-methyl-3-hydroxy-4,5-di- (hydroxymethyl) pyridine hydrochloride
M.v.205.5
II

+

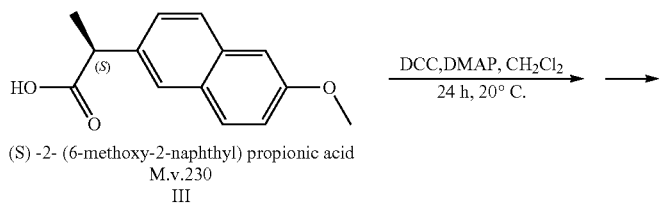

(S) -2- (6-methoxy-2-naphthyl) propionic acid
M.v.230
III

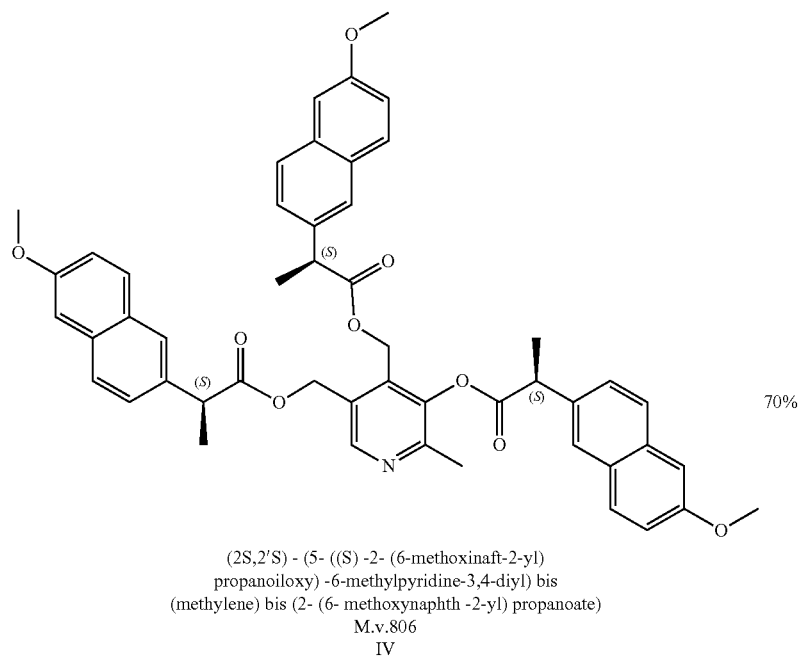

70%

(2S,2′S) - (5- ((S) -2- (6-methoxinaft-2-yl) propanoiloxy) -6-methylpyridine-3,4-diyl) bis (methylene) bis (2- (6- methoxynaphth -2-yl) propanoate)
M.v.806
IV

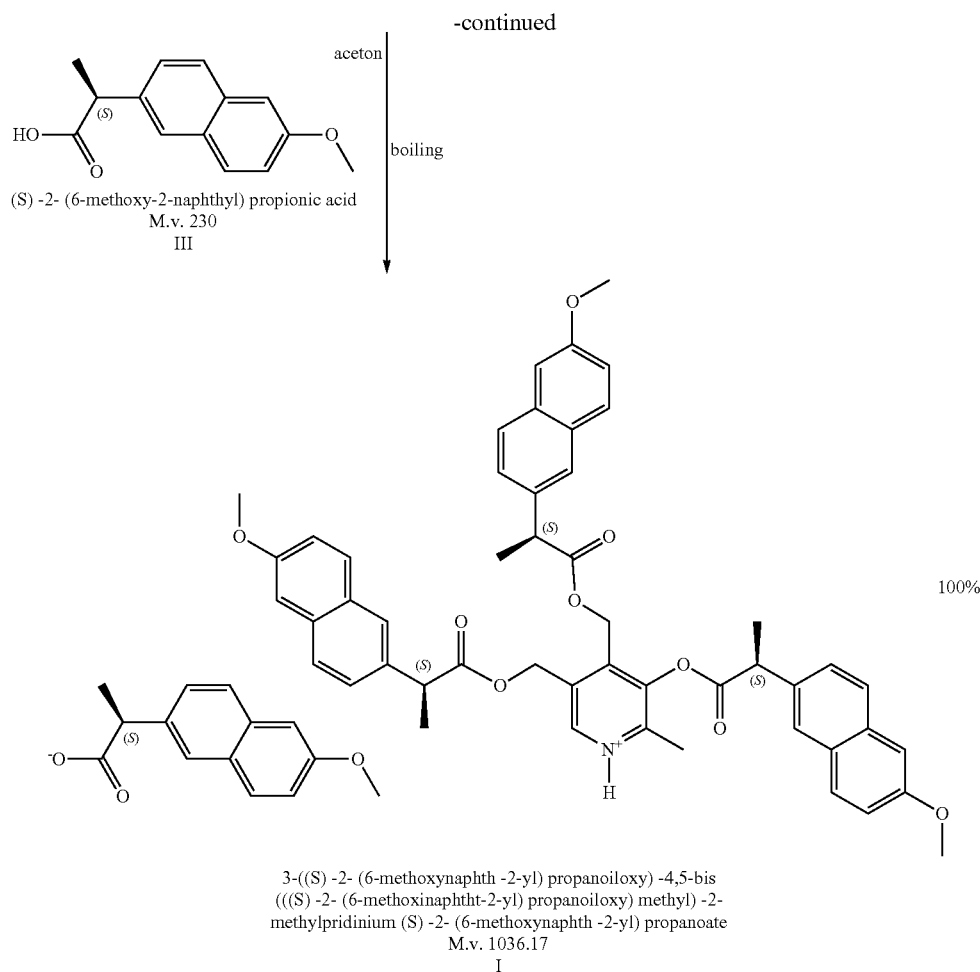

3-((S) -2- (6-methoxynaphth -2-yl) propanoiloxy) -4,5-bis
(((S) -2- (6-methoxinaphtht-2-yl) propanoiloxy) methyl) -2-
methylpridinium (S) -2- (6-methoxynaphth -2-yl) propanoate
M.v. 1036.17
I Figure Caption:
I—3-((S)-2-(6-methoxynaphth-2-yl) propanoiloxy)-4,5-bis (((S)-2-(6-methoxinaphtht-2-yl) propanoiloxy) methyl)-2-methylpyridinium (S)-2-(6-methoxynaphth-2-yl) propanoate II—2-methyl-3-hydroxy-4,5-di-(hydroxymethyl) pyridine hydrochloride III—(S)-2-(6-methoxy-2-naphthyl) propionic acid IV—(2S,2'S)-(5-((S)-2-(6-methoxinaft-2-yl) propanoiloxy)-6-methylpyridine-3,4-diyl) bis (methylene) bis (2-(6-methoxynaphth-2-yl) propanoate)

Example 1. Obtaining (2S,2'S)-(5-((S)-2-(6-methoxinaphth-2-yl) propanoiloxy)-6-methylpyridine-3,4-diyl) bis (methylene) bis (2-(6-methoxinaphtht-2-yl) Propanoate) (Compound IV)

The round bottom flask is loaded with 28.35 g of pyridoxine hydrochloride II, 95.23 g of naproxene III, 50.52 g of 4-N, N-dimethylaminopyridine and 123.73 g of dicyclohexyl carbodiimide in 5 l of acetone. The reaction mixture is stirred until the formation of the dicyclohexyl urea precipitate is stopped, then the precipitate is filtered, washed with 200 ml of acetone and the combined leachate is evaporated in a vacuum. The product is purified with column chromatography on silica gel (eluent ethyl acetate-petroleum ether 1:1). Product IV is obtained in the form of white crystalline substance (yield 82.0 g, 74%). In more detail, the preparation of this compound and its properties are described in the invention under the patent RU 2513098.

Example 2. Preparation of 3-((S)-2-(6-methoxinaphth-2-yl) propanoiloxy)-4,5-bis (((S)-2-(6-methoxinaphtht-2-yl) propanoiloxy) methyl)-2-methylpyridinium (S)-2-(6-methoxinaphth-2-yl) Propanoate (Compound I)

Put 82.0 g of compound IV in a round bottom flask, add 1 l of acetone and stir the mixture for 10 minutes. To the resulting solution add 18.22 g of (S)-2-(6-methoxy-2-naphthyl) propionic acid (naproxene) III and stir until the precipitate is completely dissolved. Acetone is removed in vacuum on the rotary evaporator (90 rpm, residual pressure 10 mbar, temperature 40° C.). The precipitate is collected and dried under vacuum on a rotary evaporator (90 rpm, residual pressure 10 mbar, temperature 80° C.). The yield of the claimed compound I is 100.1 g (99.9%).

Melting T is 145° C. $[\alpha]^{24}_D$=+22.8° (c=3.01, $CH_2Cl_2$). Absorption spectra of solutions of formula I compounds are measured in acetonitrile and methylene chloride in the wave length range from 200 to 450 nm, in which case they have maximum absorption at 262, 272, 317 and 332 nm. Deviations of the position of the maxima are ±2 nm. Concentration of solutions is 40 µg/ml. The following signals are observed in the $^1$H NMR spectrum (400 MHz, CDCl$_3$, δ, ppm, J/Hz): 1.33 (br d, 3H, CH$_3$, $^3$J=3.7); 1.40 (d, 3H, CH$_3$, $^3$J=7.1); 1.50 (d, 6H, 2CH$_3$, $^3$J=7.1); 1.90 (br s, 3H, CH$_3$); 3.47 (br s, 1H); 3.65 (k, 1H, CH, $^3$J=7.1); 3.74-3.87 (m, 13H); 4.50 (br s, 1 N); 4.80 (br s, 1 N); 4.95 and 5.04 (AB, 2H, CH$_2$, $^2$J=−12.8); 6.95-7.66 (m, 20 N), 8.19 (s, 1H, CH). The following signals are observed in the $^{13}$C NMR spectrum (100 MHz, CDCl$_3$, δ, ppm): 17.96; 18.42; 18.52; 18.92; 45.02; 45.34; 45.38; 55.40; 57.13; 61.65; 105.66; 105.73; 119.09; 119.13; 119.18; 119.38; 125.96; 126.09; 126.16; 126.20; 126.38; 126.57; 127.30; 127.36; 127.49; 128.96; 129.01; 129.39; 129.64; 133.78; 133.81; 133.86; 134.05; 134.13; 135.18; 135.21; 135.42; 136.16; 144.78; 147.16; 152.75; 157.74; 157.79; 157.96; 171.95; 174.02; 179.30.

The target substance I is a salt of compound IV with naproxen. In this regard, under the conditions of reversed-phase HPLC (table 1) it appears on the chromatogram as two peaks corresponding to compound IV and naproxen, the mass spectra of which correspond to the calculated and literature data (806.3324 and 229.0870, respectively).

The Study of the Acute Toxicity of Formula I Compound

The experiment was performed according to the fixed dose method in Wistar rats of both sexes, 6 animals per group. The initial dose for intragastric administration was 5000 mg/kg. The solvent used was a 0.5% Tween-80 solution (Tween 80—polyoxyethylene, a derivative of sorbitan and oleic acid, a commercially available polymer), which was prepared by dissolving 0.5 g of Tween-80 in 100 ml of distilled water.

To prepare a dose of 5000 mg/kg 25 g of the test compound were weighed in polystyrene boats on scales Vibra (Shinko Denshi, Japan, cat. No AF225DRCE), transferred to a 100 ml measuring flask with accuracy class A, adjusted to 100 ml with 0.5% water solution of Tween-80 and the suspension of the preparation was stirred using a dispersant SilentCrusher (Heidolph, Germany, P/N 595-06000-00-3) to a homogeneous consistency.

The introduction was carried out to animals deprived of food (for a period of not less than 8 hours) with free access to water. The volume of administration was calculated individually for each animal, based on the body mass recorded immediately before the introduction of the substance. Access to the feed was renewed an hour after the introduction. Animals were observed individually after administration for 30 minutes, then at least once per hour for 4 hours, then daily once a day for 14 days. Body mass was recorded immediately before the administration of the preparation to calculate the volume of administration, then once every two days. If the animal died during the study, the time of death was determined and documented as accurately as possible. The animal was weighed and dissected as soon as possible. Dying animals were weighed, euthanized and dissected. Animals were euthanized by inhalation of carbon dioxide. Toxic doses $LD_{10}$, $LD_{16}$, $LD_{50}$ and $LD_{84}$ were calculated using probit analysis with IBM SPSS Statistics software.

When administered intragastrically with a dose of 5000 mg/kg, a slight inhibition of the activity of the animal was observed. In 20-30 minutes this symptom disappeared. After 1.5-2 hours, animals began to take food and water. Three days later 1 rat (female) fell dead. Further throughout the study there were no mortality cases.

Throughout the experiment, all the main indicators of vital activity in experimental animals corresponded to the norm and did not differ from the control ones. The animals had a good appetite, shiny coat, visible mucous membranes were pale pink in color, the behavior corresponded to this species of animal, no abnormalities were observed during the observation period. The rats' body mass in 2 and 4 days after the start of the experiment increased by (1-4) % and (2-6) %, respectively, which approximately corresponds to the weight gain in the rats of the control group. On the eighth day of the study the weight of animals increased by (2-8) %. At the end of the experiment, the weight increase was (5-13) %. Acute toxicity parameters are presented in table 2.

TABLE 2

Acute toxicity of formula I compound with intragastric administration

| Animal species | Sex | Dose, mg/kg | Number of animals in the group/ number of dead animals | $LD_{10}$ | $LD_{16}$ | $LD_{50}$ | $LD_{84}$ |
|---|---|---|---|---|---|---|---|
| rat | males | 5000 | 6/0 | >5000 | >5000 | >5000 | >5000 |
|  | females | 5000 | 6/1 | >5000 | >5000 | >5000 | >5000 |

At the end of the experiment, euthanasia and pathomorphological dissection of control and experimental animals were performed. No changes were observed during the autopsy of rats. Corpses of animals were of the correct constitution, with average or above average fatness. Natural openings: the mouth is closed, the tongue is in the mouth, the mucous membrane of the lips and the gums are pale pink, smooth and shiny. Nasal openings—mucous membrane is pale pink, dry, no efflux, permeability is good. Ear shells are unchanged; the external auditory canal is clean. Anus is closed, mucous membrane is pale pink. The hair is kept well, the fleece is shiny. The skin is elastic; the subcutaneous fiber is well expressed, has yellowish color and is elastic. The muscles are reddish, well developed, tendons and ligaments are white, elastic and durable. The configuration of bones and joints is not broken. The position of the organs of the thoracic and abdominal cavity is anatomically correct. There is no fluid in the thoracic and abdominal cavities. The patency of the pharynx and esophagus is not broken. The heart is not changed in volume. The cavities of the heart contain a small amount of non-clotted blood; the endocardium is smooth and shiny. The lungs are of pale pink color, evenly colored, with no signs of swelling, the lobulation is well expressed. The spleen is not enlarged, with sharp edges, oblong in shape, has elastic consistency, red-brown in color. The liver is not enlarged, with sharp edges, the shape is not changed, the consistency is dense, and the color is red-brown. The stomach contains a gray feed mass of a uniform consistency. The mucous membrane of the stomach is pale gray. The mucous membrane of the thin and thick parts of the intestine is of pale pink or pale gray color. The kidneys are bean-shaped, dark brown in color, in the paranephric body there is a moderate amount of fat, the capsule is easily separated, and the boundary between the cortical and brain zones is expressed. The urinary bladder is empty or filled up with urine of light yellow color, the mucous membrane is of pale pink color. Genitals are without abnormalities. Males' testicles are of elastic consistency, are in the cavity of the scrotum, have an elliptical shape. The females have normal ovaries and uterus. The brain is not edematic; the brain matter is elastic, without hemorrhages.

Thus, the conducted studies showed that the claimed compound of the formula I after intragastric administration belongs to the 4th hazard class, i.e. to low-hazard substances (GOST 12.1.007-76 "Harmful substances. Classification and general safety requirements") and its safety in terms of $LD_{50}$ lethal dose exceeds most NSAIDs known to date (Table 3). For example, the claimed compound is 8 times less toxic than naproxen.

TABLE 3

Comparative characteristics of the compound of formula I and some known NSAIDs *

| The drug | $ED_{50}$ (mg/kg) acute inflammation | $UD_{50}$ (mg/kg) | $LD_{50}$ (mg/kg) | $UD_{50}/ED_{50}$ (safety index) | $LD_{50}/ED_{50}$ (therapeutic index) |
| --- | --- | --- | --- | --- | --- |
| Compound of formula I | 19 | >2000 | >5000 | >105 | >263 |
| Ibuprofen | 48 | 310 | 750 | 6.45 | 16 |
| Diclofenac sodium | 8 | 48 | 370 | 6 | 46 |
| Naproxen | 15 | 49 | 620 | 3.2 | 42 |
| Pyroxicam | 20 | 36 | 290 | 1.8 | 15 |
| Phenylbutazone | 56 | 120 | 430 | 2.1 | 7.7 |
| Acetylsalicylic acid | 98 | 240 | 1600 | 2.45 | 16 |
| Indomethacin | 10 | 10 | 47 | 1 | 4.7 |

* Guidelines for Pre-clinical Drug Research. Part one/edited by A. N. Mironov. - M.: Grif and K Publ., 2012. p. 944.

Gastric Toxicity of Formula I Compound

In the study of gastric toxicity were taken female and male Wistar rats aged 6-7 weeks, with a body mass of 180-220 g. The number of animals in each group was 10.

The compound of formula I was administered once intragastrically to rats deprived of food for 16 hours before the study. Three hours after the administration of the suspension of the test substance at a dose of 2000 mg/kg (in 0.5% aqueous solution of Tween-80), the animals were euthanized; their stomachs were removed, dissected along the lesser curvature, and washed in physiological solution to remove the contents.

Evaluation of gastric toxicity was performed on a 4-point scale:
  0—no damage;
  0.5—hyperemia;
  1—single minor injuries (1 or 2 point hemorrhages);
  2—multiple injuries (erosion, spot hemorrhages);
  3—significant and multiple injuries of the mucosa (erosion, hemorrhage);
  4—gross injuries covering the entire surface of the mucosa (massive hemorrhages, erosion, perforations).

According to the results of the assessment, $UD_{50}$ was determined the dose of the tested substance causing gastrotoxic (ulcerogenic) effect corresponding to 2 points.

To prepare a dose of 2000 mg/kg, 32.0 g of the formula 1 compound were weighed in polystyrene boats on scales Vibra (Shinko Denshi, Japan, cat. No. AF225DRCE), transferred to a 400 ml measuring flask with accuracy class A, adjusted to 400 ml with 0.5% water solution of Tween-80 and the suspension of the preparation was stirred using a dispersant SilentCrusher (Heidolph, Germany, P/N 595-06000-00-3) to a homogeneous consistency. The introduction to rats is carried out in the amount of no more than 5 ml/200 g.

Animals were euthanized by carbon dioxide inhalation method.

At a single introduction of formula I compound at a dose of 2000 mg/kg, the gastrotoxic effect corresponded to an average of 0.6 points in male rats and 0.4 in females (Table 4).

TABLE 4

Gastric toxicity of formula I compound with single administration at a dose of 2000 mg/kg;

| Group | Number of animals | Dose, mg/kg | Gastrotoxic effect (averaged), points males | Gastrotoxic effect (averaged), points females | $UD_{50}$ (mg/kg) males | $UD_{50}$ (mg/kg) females |
| --- | --- | --- | --- | --- | --- | --- |
| Compound of formula I | 10/10 | 2000 | 0.6 | 0.4 | >2000 | >2000 |

Thus, for a compound of formula I, the $UD_{50}$ value is >2000 mg/kg, which exceeds the similar parameter for most NSAIDs (Table 3). For example, the claimed compound is 40 times less toxic than naproxen.

Anti-Inflammatory Activity of the Compound of Formula I In Vitro

The structural enzyme cyclooxygenase 1 (COX 1) is expressed in various cell types and is involved in ensuring their normal (physiological) functional activity. Cyclooxygenase 2 (COX 2) is responsible for the synthesis of prostaglandins in severe inflammation conditions.

The analysis of COX activity consisted in measuring the peroxidase activity of cyclooxygenase. During the reaction of PGG2 (prostaglandin G2) with ADHP (10-acetyl-3,7-dihydrofenoxazine), presented in the kit used ("Cyclooxygenase (COX) Activity Assay Kit (Fluorometric)" (Biovision, cat # K 549-100) as a COX probe, a fluorescent component resorufin is formed, the absorption wavelength of which is 530-540 nm, the emission wavelength is (585-595) nm. The fluorescence intensity is directly proportional to the residual activity of COX in the sample. Skin fibroblast cells (HSF) were selected as a source of cyclooxygenase enzyme. The fibroblast cell lysate was shown to have a COX activity of 2.131 µU/mg.

Preparation of Cell Lysate.

The cells of the skin fibroblasts ($2-6 \times 10^6$) are washed once with 10 ml of phosphate buffer. The cells are resuspended in 5 ml of buffer and transferred to a 15 ml tube. They are centrifuged at 1500 g for 4 minutes. The supernatant is then poured, the cell pellet is resuspended in 0.5-1 ml of cold lysing buffer with a protease cocktail (approximately 0.4 ml of buffer per 100 µl of cell pellet), and centrifuged at 4° C. for 15 minutes at 10,000 g. The supernatant is separated and used as a source of COX.

Preparation of Reagents.

COX cofactors are dissolved 200 times by adding 2 μl of cofactors to 398 μl of buffer immediately before use. 65 μl of arachidonic acid and 65 μl of NaOH are mired, and then diluted 10 times with 1170 μl of distilled water. The solution is stable for 1 hour.

The reaction mixture is prepared (for 2 parallel wells) by mixing the following reagents indicated below:
COX probe—2 μl;
dissolved cofactor—4 μl (stable for 1 hour);
cell lysate—20 μl;
with the help of COX buffer the volume is brought to 172 μl.

Preparation of the Tested Substances:

Naproxen stock solutions and substances of the formula I in dimethyl sulfoxide (DMSO) with a concentration of 1000 μM are used to prepare preliminary dilutions in 2-step increments. Respectively, 5 concentrations from 62.5 to 1000 μM are obtained.

Using a multichannel pipette, reagents are added to the appropriate plate wells: first, the reaction mixture, then the solutions of the test substances in DMSO in a series of concentrations and control substances (inhibitor COX 1 SC560 and inhibitor COX 2 Celecoxib), pure solvent DMSO (for wells with higher activity). Two replications are used. They are incubated for 5 minutes.

Initiating a Reaction.

Before the start of the reaction, a single fluorescence measurement is performed in all wells of the plate to account for the own signal of the test and control substances. Then 10 μl of arachidonic acid solution is added to all wells of the plate using a multichannel pipette to initiate the reaction. After adding arachidonic acid, the fluorescence (Ex/Em=535/587 nm) is immediately measured in kinetic mode every 15 seconds for 30 minutes.

The fluorescence parameter of images with control and tested substances is calculated according to the formula:

$$\text{Average Net RFU} = \text{Average RFU} - \text{Average Blank RFU}$$

The percentage of COX inhibition is calculated according to the formula:

$$\left(1 - \frac{\text{Average Net Inhibitor RFU}}{\text{Average Net RFU for non-inhibited}}\right) \times 100$$

Further, using the available data points for the test substance and the reference substance (naproxen), we construct the most suitable sigmoid inhibition curve. Based on this curve, the $IC_{50}$ of the test sample for COX is calculated.

According to the recommendations of the manufacturer of the kit used, the COX-1 inhibitor SC560 and the COX-2 inhibitor celecoxib are added to the reaction mixture in a volume of 2 μl (this amount is sufficient to completely inhibit the appropriate isoform). The residual activity of COX contained in cell lysate after treatment by SC560 and celecoxib is 72.8% and 32.0% respectively.

In the study of inhibitory activity, the concentration of naproxen and the tested substance in the well is from 1.25 to 20 μM.

To determine the proportion of inhibition by the preparation of each of the isoforms, the studied substances are tested in a concentration pattern in the presence of a selective inhibitor COX 1 SC560, as well as in the presence of a selective inhibitor COX 2 celecoxib. The inhibitor is added in sufficient quantities to completely inhibit the corresponding isoform of the enzyme, while the other isoform remains active.

Conventionally assuming the activity in the presence of only the test preparation as 100%, the residual activity of COX 1 and COX 2 and the percentage of inhibition of each isoform by the preparation are calculated. The compound of formula I exhibits preferential inhibitory activity against the isoform of COX-2.

Thus, the naproxen $IC_{50}$ (prototype) is 9.56 μM, which is 1.25 times the $IC_{50}$ of the compound of formula I, equal to 7.7 μM. From the above, it can be concluded that the claimed compound of formula I is more effective as a cyclooxygenase inhibitor, since it acts at a lower concentration.

Anti-Inflammatory Activity of the Compound of Formula I In Vivo

The experiment was carried out using female and male Wistar rats aged 6-7 weeks with a body mass of 180-220 g. The number of animals in each group was 10.

The acute inflammatory reaction (edema) was reproduced by subplantar (under plantar or plantar aponeurosis) administration of 0.1 ml of 1% carrageenin solution (sulfated polysaccharide from Irish sea moss). The severity of the inflammatory reaction was assessed 3 hours after the induction of inflammation by a change in the volume of the paw (oncometric). The substance of formula I was administered into the stomach with the probe 1 hour before the introduction of the 1% solution of carrageenin. A 0.5% Tween-80 solution was used as a negative control. The anti-inflammatory effect, assessed by a decrease in edema, was expressed as a percentage of the control. According to the results of the action of four doses of the analyte, the calculation of $ED_{50}$ was performed.

To prepare a dose of 50 mg/kg, 1000 mg of the formula I compound were weighed in polystyrene boats on scales Vibra (Shinko Denshi, Japan, cat. No AF225DRCE), transferred to a 200 ml measuring flask with accuracy class A, adjusted to 200 ml with 0.5% water solution of Tween-80 and the suspension of the preparation was stirred using a dispersant SilentCrusher (Heidolph, Germany, P/N 595-06000-00-3) to a homogeneous consistency. The introduction to rats was carried out in the amount of no more than 1 ml/100 g. The concentration of the resulting solution was 5 mg/ml.

To prepare a dose of 20 mg/kg, 40 ml of solution with a concentration of 5 mg/ml (50 mg/kg) were taken, transferred to a 100 ml measuring flask with accuracy class A, adjusted to 100 ml with 0.5% water solution of Tween-80 and the suspension of the preparation was stirred using a dispersant to a homogeneous consistency.

To prepare a dose of 10 mg/kg, 20 ml of solution with a concentration of 5 mg/ml (50 mg/kg) were taken, transferred to a 100 ml measuring flask with accuracy class A, adjusted to 100 ml with 0.5% aqueous solution of Tween-80 and the suspension of the preparation was stirred with a magnetic stirrer MR Hei-Standard (Heidolph, Germany) to a homogeneous consistency.

To prepare a dose of 5 mg/kg, 4 ml of solution with a concentration of 5 mg/ml (50 mg/kg) were taken, transferred to a 100 ml measuring flask with accuracy class A, adjusted to 100 ml with 0.5% water solution of Tween-80 and the suspension of the preparation was stirred with a magnetic stirrer to a homogeneous consistency.

Animals were observed individually after administration for 30 minutes, then at least once an hour for 4 hours. Body mass was recorded just before the administration of the preparation to calculate the volume of administration.

Animals were euthanized by inhalation of carbon dioxide.

When a dose of 50, 20, 10 and 5 mg/kg of the compound of formula I was administered to male rats, inflammatory edema decreased by 62.34, 51.25, 23.57 and 12.39%, respectively, in contrast to the control group. In female rats, with a dose of 50, 20, 10 and 5 mg/kg of the compound of formula I administered, the edema decreased by 65.47, 67.89, 38.64 and 13.37%, respectively. The results are presented in table 5.

TABLE 5

Effect of the compound of formula I on acute exudative inflammation after intragastric administration

| Group | Dose, mg/kg | Paw volume 0 | Paw volume 3 h | Anti-inflammatory effect, % |
|---|---|---|---|---|
| Male rats | | | | |
| Compound of formula I | 50 mg/kg | 1.04 ± 0.20 | 1.54 ± 0.45 | 37.66 ± 19.16 |
| | 20 mg/kg | 0.93 ± 0.05 | 1.51 ± 0.16 | 48.75 ± 16.39 |
| | 10 mg/kg | 0.93 ± 0.06 | 1.84 ± 0.23 | 76.43 ± 22.74 |
| | 5 mg/kg | 0.89 ± 0.07 | 1.87 ± 0.21 | 87.61 ± 19.75 |
| Control (Tween-80) | — | 0.98 ± 0.09 | 2.23 ± 0.31 | 100.00 ± 16.92 |
| Female rats | | | | |
| Compound of formula I | 50 mg/kg | 0.91 ± 0.05 | 1.26 ± 0.23 | 34.53 ± 18.52 |
| | 20 mg/kg | 0.91 ± 0.09 | 1.23 ± 0.20 | 32.11 ± 15.06 |
| | 10 mg/kg | 0.96 ± 0.06 | 1.60 ± 0.16 | 61.36 ± 17.12 |
| | 5 mg/kg | 1.00 ± 0.03 | 1.94 ± 0.20 | 86.63 ± 17.71 |
| Control (Tween-80) | — | 0.86 ± 0.10 | 1.80 ± 0.28 | 100.00 ± 19.39 |

According to the results of statistical processing of the obtained data the $ED_{50}$ of the compound of formula I on males is 23 mg/kg, on females is 14 mg/kg. The mean value of $ED_{50}$ without sex distinction is 18.5 (~19) mg/kg.

According to the literature, $ED_{50}$ of naproxen is 15 mg/kg, ibuprofen—48 mg/kg, diclofenac sodium—8 mg/kg, pyroxicam—20 mg/kg, phenylbutazone—56 mg/kg, indomethacin –10 mg/kg, acetylsalicylic acid—98 mg/kg [Guidelines for Pre-clinical Drug Research. Part one/edited by A. N. Mironov. —M.: Grif and K Publ., 2012. p. 944]. Thus, the applicant experimentally proved the presence of a high anti-inflammatory activity of a compound of formula I, which is superior in its value (in four cases out of seven) or comparable to the anti-inflammatory activity of modern NSAIDs.

Analgesic Effect of Formula I Compound

In the study of analgesic properties of the formula I compound, were taken female and male Wistar rats aged 6-7 weeks with a body mass of 180-220 g. The number of animals in each group was 10.

Chronic immune inflammation was modeled in rats by subplantar administration of 0.1 ml of a 1% solution of carrageenin (a sulfated polysaccharide from Irish sea moss) into the right hind paw. The substance was administered intragastrically using a gastric probe. Naproxen was used as a comparison drug, 0.5% Tween-80 solution was used as a negative control. The anti-inflammatory effect, assessed by a decrease in edema, was expressed as a percentage relative to the control; according to the results of the action of four doses of the test substance, the calculation of $ED_{50}$ was performed.

Inflammatory hyperalgesia (increased pain sensitivity of inflamed tissues in rats) was caused by carrageenin and was assessed by decrease of the pain sensitivity threshold—PST (by PST difference) to mechanical irritation (squeezing) of the paw tissue of the animal before the introduction of carrageenin and 3 hours after it. The measurement was performed on the inflamed paw. Used analgesimeter Ugo Basile S.R.L. (Italy) provides a gradual increased afterload on the rat's inflamed paw until a pain reaction appears (assessed by squeaking of animal or withdrawing the paw). The analyte was administered 2 h after carrageenin administration. The analgesic effect with evaluation of $ED_{50}$ was assessed by a decrease in hyperalgesia 1 h after intragastric administration of the analyte. An increase in the pain response threshold under the influence of the substances under study was expressed in an increase in the force of compression of the limb and characterized the intensity of the analgesic effect of the preparation. After the experiment, animals were euthanized by carbon dioxide inhalation method.

To prepare a dose of 50 mg/kg, 1000 mg of the formula I compound were weighed in polystyrene boats on scales Vibra (Shinko Denshi, Japan, cat. No AF225DRCE), transferred to a 200 ml measuring flask with accuracy class A, adjusted to 200 ml with 0.5% water solution of Tween-80 and the suspension was dispersed using a dispersant Silent-Crusher (Heidolph, Germany, P/N 595-06000-00-3) to a homogeneous consistency. The introduction to rats was carried out in the amount of no more than 1 ml/100 g. The concentration of the resulting solution was 5 mg/ml.

To prepare a dose of 20 mg/kg, 40 ml of solution with a concentration of 5 mg/ml (50 mg/kg) were taken, transferred to a 100 ml measuring flask with accuracy class A, adjusted to 100 ml with 0.5% water solution of Tween-80 and the suspension was dispersed to a homogeneous consistency using a dispersant.

To prepare a dose of 10 mg/kg, 20 ml of solution with a concentration of 5 mg/ml (50 mg/kg) were taken, transferred to a 100 ml measuring flask with accuracy class A, adjusted to 100 ml with 0.5% aqueous solution of Tween-80 and the suspension was stirred to a homogeneous consistency with a magnetic stirrer MR Hei-Standard (Heidolph, Germany).

To prepare a dose of 5 mg/kg, 4 ml of solution with a concentration of 5 mg/ml (50 mg/kg) were taken, transferred to a 100 ml measuring flask with accuracy class A, adjusted to 100 ml with 0.5% water solution of Tween-80 and the suspension was stirred to a homogeneous consistency with a magnetic stirrer.

The results of the experiment are presented in table 6.

TABLE 6

Analgesic effect of compound of formula I on rats

| Group | Sex | Dose, mg/kg | Paw volume 0 hours | Paw volume 3 hours | Analgesic effect, % | Analgesic effect, total/analgesic effect |
|---|---|---|---|---|---|---|
| Compound of formula I | males | 50 | 3.4 ± 2.3 | 10.6 ± 6.3 | 367.9 ± 220.1 | 10/8 |
|  | females |  | 8.9 ± 5.7 | 12.4 ± 6.5 | 484.4 ± 251.8 | 10/7 |
|  | males | 20 | 6.4 ± 5.7 | 12.0 ± 6.2 | 418.1 ± 215.7 | 10/9 |
|  | females |  | 4.6 ± 3.3 | 9.1 ± 7.4 | 353.5 ± 289.7 | 10/9 |
|  | males | 10 | 4.2 ± 2.4 | 12.0 ± 4.6 | 453.7 ± 159.9 | 10/10 |
|  | females |  | 4.3 ± 2.2 | 10.5 ± 7.2 | 408.2 ± 279.3 | 10/8 |
|  | males | 5 | 4.4 ± 2.7 | 5.5 ± 2.5 | 259.9 ± 229.7 | 10/7 |
|  | females |  | 3.9 ± 1.4 | 7.2 ± 3.2 | 282.0 ± 125.9 | 10/9 |
| Control | males | 0 | 5.7 ± 2.0 | 2.9 ± 0.9 | 100.0 ± 30.0 | 10/10 |
|  | females |  | 4.7 ± 1.5 | 2.6 ± 1.4 | 100.0 ± 52.6 | 10/9 |
| Naproxen | males | 15 | 5.0 ± 2.9 | 6.7 ± 4.6 | 234.5 ± 160.2 | 10/7 |
|  | females |  | 5.0 ± 6.2 | 5.0 ± 3.2 | 195.3 ± 125.3 | 10/7 |

From the presented results, it follows that the claimed compound of formula I exhibits a pronounced anesthetic effect already at a dose of 5 mg/kg, while naproxen (prototype) has a similar effect only at a dose of 15 mg/kg, which is a demonstrative fact of its higher efficiency. Thus, the therapeutic index ($LD_{50}/ED_{50}$) of the claimed compound in terms of its analgesic activity is more than 1000 against 42 for naproxen, and the safety index ($UD_{50}/ED_{50}$) is more than 400 against 3.2 for naproxen.

Antipyretic Effect of Compound of Formula I on Rats

In the study of antipyretic properties of the formula I compound, were taken female and male Wistar rats aged 6-7 weeks, with a body mass of 180-220 g. The number of animals in each group was 10.

The febrile reaction was caused by subcutaneous administration of a 20% suspension of baking yeast. The rectal temperature was measured with an electrothermometer prior to the introduction of yeast and 18 hours after it (the difference of these measurements is the estimated hyperthermic reaction). The preparation was administered to animals at the peak of hyperthermia once (after 18 hours). The antipyretic effect was evaluated by hyperthermia decrease 2 hours after the injection of the test substance, and then the effect dynamics was recorded at hourly intervals for 7 hours.

To prepare a dose of 75 mg/kg, 1500 mg of the formula I compound were weighed in polystyrene boats on scales Vibra (Shinko Denshi, Japan, cat. No AF225DRCE), transferred to a 200 ml measuring flask with accuracy class A, adjusted to 200 ml with 0.5% water solution of Tween-80 and the suspension of the preparation was stirred to a homogeneous consistency using a dispersant SilentCrusher M (Heidolph, Germany). The introduction to rats was carried out in the amount of no more than 1 ml/100 g. The concentration of the resulting solution was 7.5 mg/ml.

To prepare a dose of 50 mg/kg, 66.7 ml of solution with a concentration of 7.5 mg/ml (75 mg/kg) were taken, transferred to a 100 ml measuring flask with accuracy class A, adjusted to 100 ml with 0.5% water solution of Tween-80 and the suspension of the preparation was stirred to a homogeneous consistency using a dispersant.

To prepare a dose of 20 mg/kg, 26.7 ml of solution with a concentration of 7.5 mg/ml (75 mg/kg) were taken, transferred to a 100 ml measuring flask with accuracy class A, adjusted to 100 ml with 0.5% aqueous solution of Tween-80 and the suspension of the preparation was stirred to a homogeneous consistency with a magnetic stirrer MR Hei-Standard (Heidolph, Germany). The difference in temperature after preparation administration and after 18 hours of induction with yeast was taken as the parameter of hyperthermia decrease.

Animals were observed individually after administration throughout the study. Body mass was recorded just before the administration of the preparation to calculate the volume of administration. Descriptive statistics were used for all data: there were calculated the average value and the standard error of the mean, results were represented in the final table 7. Wilcoxon nonparametric criterion was used for statistical comparison of experimental groups. Differences were determined at the 0.05 level of significance. The statistical analysis was carried out using the R-studio program. The results of the study of antipyretic effects of various doses of formula I compound are presented in table 7.

TABLE 7

The antipyretic activity of the formula I compound

| Group | Dose, mg/kg | Sex of animals | Δ t after 2 hours, (M ± SD) | Δ t after 3 hours, (M ± SD) | Δ t after 4 hours, (M ± SD) | Δ t after 5 hours, (M ± SD) | Δ t after 6 hours, (M ± SD) | Δ t after 7 hours, (M ± SD) |
|---|---|---|---|---|---|---|---|---|
| Compound of formula I | 20 | Males | 0.13 ± 0.31 | 0.24 ± 0.37 | 0.02 ± 0.25 | 0.1 ± 0.26 | −0.21 ± 0.22 | 0.04 ± 0.28 |
|  |  | Females | −0.07 ± 0.17 | −0.27 ± 0.17 | −0.35 ± 0.16 | 0.34 ± 0.18 | −0.01 ± 0.22 | −0.08 ± 0.19 |
|  | 50 | Males | 0.22 ± 0.16 | 0.36 ± 0.17* | 0.39 ± 0.11* | 0.25 ± 0.2 | 0.11 ± 0.19 | 0.09 ± 0.18 |
|  |  | Females | 0.87 ± 0.09* | 0.91 ± 0.14* | 0.66 ± 0.12* | 0.53 ± 0.14* | 0.61 ± 0.22* | 0.5 ± 0.15* |
|  | 75 | Males | 0.76 ± 0.15* | 1.15 ± 0.18* | 1.38 ± 0.14* | 1.31 ± 0.25* | 0.96 ± 0.16* | 0.92 ± 0.19* |
|  |  | Females | 0.97 ± 0.19* | 0.96 ± 0.15* | 1.39 ± 0.09* | 1.52 ± 0.22* | 1.51 ± 0.17* | 1.17 ± 0.2* |

TABLE 7-continued

The antipyretic activity of the formula I compound

| Group | Dose, mg/kg | Sex of animals | Δ t after 2 hours, (M ± SD) | Δ t after 3 hours, (M ± SD) | Δ t after 4 hours, (M ± SD) | Δ t after 5 hours, (M ± SD) | Δ t after 6 hours, (M ± SD) | Δ t after 7 hours, (M ± SD) |
|---|---|---|---|---|---|---|---|---|
| Naproxen | 15 | Males | 1.39 ± 0.25* | 1.49 ± 0.21* | 1.6 ± 0.19* | 1.51 ± 0.25* | 1.53 ± 0.19* | 1.44 ± 0.24* |
|  | 15 | Females | 1.64 ± 0.23* | 1.35 ± 0.15* | 1.58 ± 0.21* | 1.21 ± 0.18* | 1.09 ± 0.25* | 0.74 ± 0.14* |
| Control | — | Males | 0.08 ± 0.18 | −0.49 ± 0.13 | −0.46 ± 0.2 | −0.68 ± 0.16 | −0.28 ± 0.2 | 0.19 ± 0.21 |
| 0.5% Tween 80 | — | Females | −0.31 ± 0.14 | −0.36 ± 0.16 | −0.42 ± 0.18 | −0.65 ± 0.2 | −0.25 ± 0.18 | −0.47 ± 0.21 |

*p < 0.05 in comparison with naproxen 18 hours after the subcutaneous introduction of baking yeast suspension a positive increase in rectal temperature was observed in groups of animals on average by 1.5° C. No decrease in temperature was observed in the control group of animals during the entire observation period (up to 7 hours after preparation administration). With the introduction of the formula I compound to both males and females at a dose of 20 mg/kg no antipyretic action was observed. When the dose was increased to 50 mg/kg, a distinct decrease in temperature was observed in the group of females—so, 2 and 3 hours after the substance was introduced, the temperature was lower than before the introduction by 0.9° C., in 4, 5, 6 and 7 hours after the introduction the decrease was (0.5-0.7) ° C.

With the introduction of formula I compound at a dose of 50 mg/kg, a significant decrease in temperature was observed in 3-4 hours after administration. The level of decrease was equal to (0.34-0.97) ° C.

The greatest effect was observed in animal groups which were administered formula I compound at a dose of 75 mg/kg. Thus, with the introduction of the substance at a dose of 75 mg/kg throughout the experiment, the temperature decreased significantly and was less than before the introduction for (0.76-1.5) ° C.

With the introduction of naproxen at a dose of 15 mg/kg (or 65 µmol/kg), the temperature also decreased significantly. The level of temperature decrease was (0.74-1.6) ° C.

Summarizing the results obtained, it should be concluded that, at a dose of 75 mg/kg, the claimed compound has antipyretic properties at the level of naproxen dose of 15 mg/kg. It should be particularly noted that in molar terms these doses do not practically differ, since the molar mass of naproxen is significantly lower than the molar mass of the compound of formula I, and is equal to 230 g/mol versus 1036 g/mol of the claimed compound. The therapeutic index ($LD_{50}/ED_{50}$) of the claimed compound in terms of its antipyretic activity is more than 67 against 42 for naproxen, and the safety index ($UD_{50}/ED_{50}$) is more than 27 against 3.2 for naproxen.

Thus, it follows from the above that the applicant obtained a new compound based on pyridoxine and naproxen-3-((S)-2-(6-methoxynaphth-2-yl) propanoyloxy)-4,5-bis (((S)-2-(6-methoxynaphth-2-yl)-propanoyloxy) methyl)-2-methylpyridinium (S)-2-(6-methoxynaphth-2-yl)-propanoate, which simultaneously has high anti-inflammatory, analgesic and antipyretic properties that are superior or comparable with similar properties of naproxen (prototype), while maintaining extremely low toxicity (including gastric toxicity).

In general, the claimed compound is 8 times less toxic and 40 times less gastrotoxic compared to naproxen (prototype).

The claimed invention meets the criterion of "novelty" applied to inventions, because from the studied level of technology, no technical solutions were found that coincide with the claimed one on essential features leading to the realization of the stated technical results, which are new pyridoxine and naproxen derivatives having low toxicity, including gastric toxicity. The claimed chemical compound expands the range of products for the treatment of rheumatic diseases, as well as diseases accompanied by inflammation, pain and fever, and is fundamentally new, unparalleled in the world in terms of its effectiveness and safety of use.

The claimed invention meets the criterion of "inventive step" applied to inventions, because it is not obvious to specialists in this field of technology, namely, from the studied level of technology no anti-inflammatory, analgesic and antipyretic drugs of the claimed structure were identified.

The claimed invention meets the criterion of "industrial applicability", as it can be implemented at any specialized enterprise using standard equipment, well-known domestic materials and technologies. The applicant obtained in the laboratory the target product—non-steroidal anti-inflammatory drug based on naproxen, with the claimed technical results and achieved all the claimed objectives.

What is claimed is:

1. A non-steroidal anti-inflammatory drug based on naproxen formula (I):

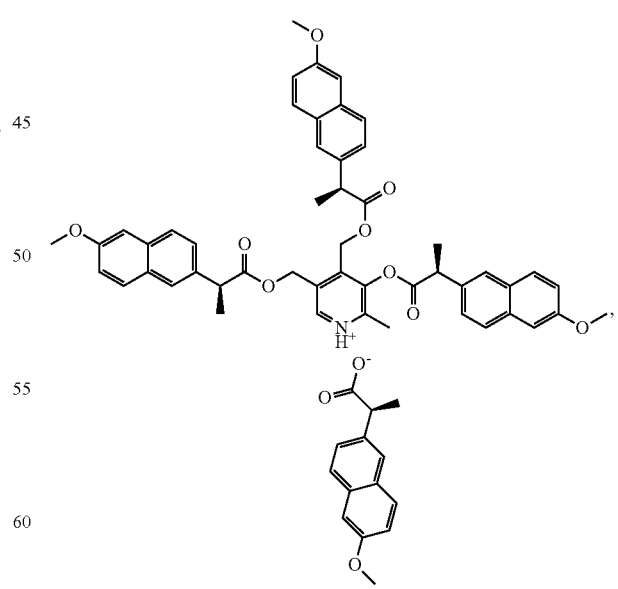

having anti-inflammatory, analgesic and antipyretic activity, as well as reduced acute toxicity and gastric toxicity.

* * * * *